(12) United States Patent
Guo et al.

(10) Patent No.: US 10,830,679 B2
(45) Date of Patent: Nov. 10, 2020

(54) DEVICE AND METHOD FOR PROCESSING SLIDE SPECIMEN THEREOF

(71) Applicant: XIAMEN TALENT BIOMEDICAL TECHNOLOGY COMPANY, LTD., Fujian (CN)

(72) Inventors: James Guo, Guangdong (CN); Derek Guo, Guangdong (CN)

(73) Assignee: XIAMEN TALENT BIOMEDICAL TECHNOLOGY COMPANY, LTD., Fujian (CN)

(*) Notice: Subject to any disclaimer, the term of this patent is extended or adjusted under 35 U.S.C. 154(b) by 260 days.

(21) Appl. No.: 16/087,106

(22) PCT Filed: Mar. 21, 2017

(86) PCT No.: PCT/CN2017/077571
§ 371 (c)(1),
(2) Date: Sep. 21, 2018

(87) PCT Pub. No.: WO2017/162149
PCT Pub. Date: Sep. 28, 2017

(65) Prior Publication Data
US 2019/0101480 A1    Apr. 4, 2019

(30) Foreign Application Priority Data

Mar. 21, 2016 (CN) .......................... 2016 1 0160797
Aug. 31, 2016 (CN) .......................... 2016 1 0798084

(51) Int. Cl.
*G01N 1/00*        (2006.01)
*G01N 1/44*        (2006.01)
(Continued)

(52) U.S. Cl.
CPC .................. *G01N 1/44* (2013.01); *B01L 7/02* (2013.01); *B01L 7/52* (2013.01); *B01L 7/54* (2013.01);
(Continued)

(58) Field of Classification Search
None
See application file for complete search history.

(56) References Cited

FOREIGN PATENT DOCUMENTS

| CN | 2837851 | 11/2006 |
|---|---|---|
| CN | 202823648 | 3/2013 |

(Continued)

OTHER PUBLICATIONS

"International Search Report (Form PCT/ISA/210)", dated Jun. 23, 2017, with English translation thereof, pp. 1-6.

*Primary Examiner* — Jyoti Nagpaul
(74) *Attorney, Agent, or Firm* — JCIPRNET

(57) ABSTRACT

A device for processing a slide specimen and a method thereof, wherein the device mainly comprises a container, a base, a heating device, a slide cover plate, a slide, a slide rack, a liquid outlet, a liquid inlet, a controller, a thermocouple, a temperature display screen, a temperature maintaining time display window and a temperature maintaining time adjustment button. A large amount of slide specimens are enable to carry out processing such as reagent loading, cleaning, heat treatment, temperature maintaining and drying in one same device, realizing that there's no need to take or transfer the slide manually during the whole process of the slide specimen processing, reducing manual intervention and interference, not only saving time but also simplifying the operation steps and reducing operation errors.

15 Claims, 6 Drawing Sheets

(51) Int. Cl.
  *B01L 7/02*      (2006.01)
  *B01L 9/00*      (2006.01)
  *G01N 1/31*      (2006.01)
  *B01L 7/00*      (2006.01)
  *C12M 3/00*      (2006.01)
  *C12M 3/06*      (2006.01)
  *C12M 1/00*      (2006.01)
  *G01N 1/30*      (2006.01)
  *G01N 1/38*      (2006.01)
  *B01L 3/00*      (2006.01)

(52) U.S. Cl.
  CPC ............... *B01L 9/52* (2013.01); *B01L 9/523* (2013.01); *B01L 9/527* (2013.01); *C12M 3/00* (2013.01); *C12M 23/16* (2013.01); *C12M 23/42* (2013.01); *C12M 23/44* (2013.01); *C12M 23/48* (2013.01); *C12M 23/58* (2013.01); *G01N 1/30* (2013.01); *G01N 1/312* (2013.01); *G01N 1/38* (2013.01); *B01L 3/50855* (2013.01); *B01L 2200/147* (2013.01); *B01L 2400/0406* (2013.01); *B01L 2400/0475* (2013.01); *B01L 2400/06* (2013.01); *B01L 2400/082* (2013.01)

(56) References Cited

FOREIGN PATENT DOCUMENTS

| | | |
|---|---|---|
| CN | 203148762 | 8/2013 |
| CN | 104089808 | 10/2014 |
| CN | 105176790 | 12/2015 |
| CN | 105628475 | 6/2016 |
| CN | 105628476 | 6/2016 |
| CN | 105675369 | 6/2016 |
| CN | 105675383 | 6/2016 |
| CN | 106226141 | 12/2016 |
| CN | 106248470 | 12/2016 |
| CN | 106353516 | 1/2017 |
| CN | 205941114 | 2/2017 |
| EP | 1291637 | 3/2003 |

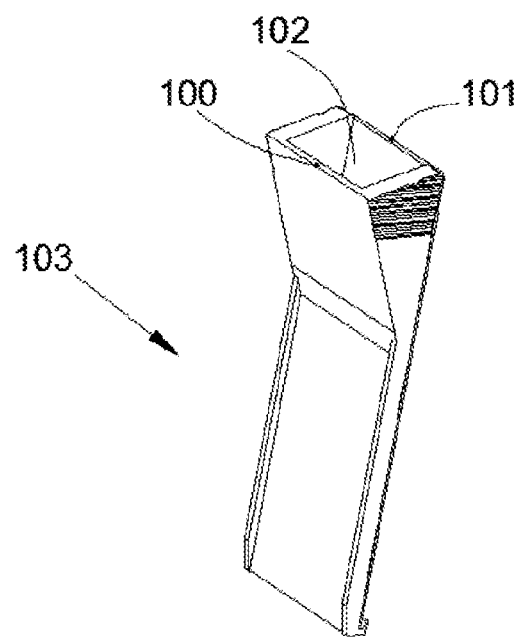
FIG. 3
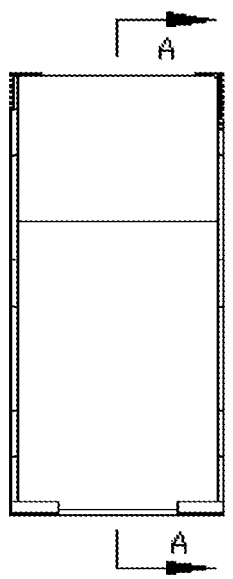 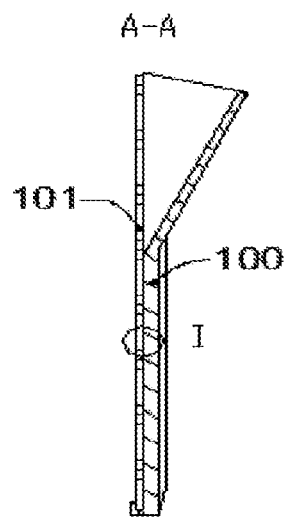 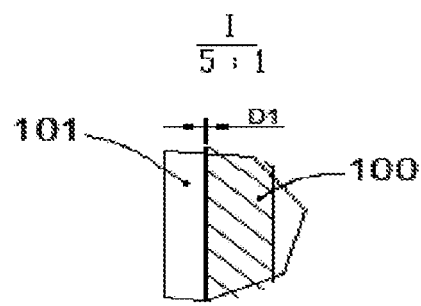
FIG. 4a  FIG. 4b  FIG. 4c

DEVICE AND METHOD FOR PROCESSING SLIDE SPECIMEN THEREOF

CROSS-REFERENCE TO RELATED APPLICATION

This application is a 371 application of an international PCT application serial no. PCT/CN2017/077571, filed on Mar. 21, 2017, which claims priority to and the benefit of China Patent Application No. CN201610160797.0, filed on Mar. 21, 2016 and China Patent Application No. CN201610798084.7, filed on Aug. 31, 2016. The entirety of each of the above-mentioned patent applications is hereby incorporated by reference herein and made a part of this specification.

TECHNICAL FIELD

The present invention belongs to a field of biological specimen processing, and specifically relates to a device and a method for processing a slide specimen.

BACKGROUND

The whole process of tests of proteins, pathogens or genes, such as by immunohistochemistry and by in-situ hybridization gene testing, on a slide specimen requires dozens of complicated steps, and accuracy of the test result thereof may be severely affected by various factors such as environment and manual operation. Simplifying an operation process and reducing an influence of environment are of the highest priority to enhance an efficiency and accuracy of specimen testing.

Currently, during the test process, a slide specimen is laid horizontally which takes a rather large space and limits the number and efficiency of the slide specimen processing.

A reagent is dispensed from the above of the slide, which could make a big position error. After adding the reagent, incubation at open may easily lead to a problem of evaporation of the reagent and drying of the specimen.

Usually, the reagent is added by dispensing from the above of the slide, and before dispensing, liquids that previously present on the slide need to be removed and the slide needs to be drained off and wiped. Such operations bring a high degree of manual error, and an amount of the residual liquid may affect a concentration and an efficacy of the reagent in the next step. The process of wiping the slide may also damage the specimen and leads to the drying of specimen that is wiped previously and thus results in a failure of the specimen processing.

During the specimen processing, a majority of specimens require a heat treatment. A majority of specimens require a heat treatment, which is a necessary step to make a characteristic protein of an antigen or the pathogen restore to an original shape, or make gene strands melt. The heating is generally performed at a temperature of 80-121° C. and maintained for 3 to 60 minutes. The most common methods are as follows: cooking in an autoclave, conventional boiling, cooking in a microwave oven or heating in water bath. However, container or shelf that is used for slide specimen processing in the manual operation at present is neither heat-resisting, nor has a heating function. During the slide specimen processing, the slide specimen needs to be transferred into a heatable container, and then transferred back to a normal-temperature operation desk, increasing the complexity of the operation process and the operation error.

The present invention achieves that the slide specimen needs not to be transferred and still remains inside the same device for processing, and there's no need to take or transfer the slide manually during the whole process of the slide specimen processing, reducing manual intervention and interference, not only saving time but also simplifying the operation steps and reducing the operation errors.

SUMMARY OF THE INVENTION

In order to solve the above problems, a device and a method for processing a slide specimen are provided, enabling a large amount of slides to be placed closely and slides to be remained in the same device from the beginning to the end, guaranteeing that the slide specimen is covered by a reagent constantly and guaranteeing a repeatability and reliability of a heat treatment.

Objectives of the present invention are achieved at least by one of the following technical solutions.

A device for processing a slide specimen, comprises a container, a base, a heating device, a slide cover plate, a slide, a slide rack, a liquid outlet, a liquid inlet, a controller, a thermocouple, a temperature display screen, a temperature maintaining time display window and a temperature maintaining time adjustment button; and the slide rack is a slide rack with single-column insertion slots or a slide rack with multi-column insertion slots.

The slide cover plate fits with the slide to assemble a set of slide assembly for specimen processing.

One or more slide racks are hung in the container; each column of the slide rack is provided with one or more V-shape insertion slots, and the V-shape insertion slots in a same column are arranged in line; a spring piece is provided inside each V-shape insertion slot; an outline of an upper end of the slide assembly matches with the V-shape insertion slot, and the slide assembly is inserted along the V-shape insertion slot of the slide rack; back of the slide cover plate presses the spring piece, and a spring pressure is generated to clamp the slide and the slide cover plate.

The heating device is located above the base and below the container; the controller controls a heating operation of the heating device performed on the container; the thermocouple is positioned inside the container; the thermocouple performs a real-time sense on a temperature in the container, and transfers a sensed temperature information to the controller to adjust a power output of the heating device, and then to adjust the temperature; the temperature display screen shows the temperature inside the container; the temperature maintaining time adjustment button can adjust and set a time for the temperature maintaining; and the temperature maintaining time display window shows a required time for the temperature maintaining.

The liquid inlet allows a heating medium or reagent stored in an external container to be added to the container quantitatively when required; the liquid outlet allows the heating medium or liquid in the container to be discharged from the container; and the liquid inlet and the liquid outlet can be connected with a micropump or a magnetic valve, and the controller controls the micropump or the magnetic valve to open or close.

Further, the slide cover plate has a rectangular plane slot, so that one capillary gap is formed between the slide and the cover plate after the slide is attached to the cover plate; a slide specimen section is stuck on a surface of the slide in the capillary gap, and a loading liquid enters the capillary gap through a reagent loading reservoir formed between the cover plate and the slide, and covers evenly on the slide specimen.

Further, the cover plate comprises a capillary plane, a depth locating face, a width locating block, a bottom locating block, a reservoir side face and a reservoir opening face; two depth locating faces are provided above two lateral sides facing toward each other of the capillary plane, and the capillary plane is parallel to the depth locating faces; portions of a plane of the slide which are close to edges of two sides are attached to the depth locating faces, so that one capillary gap is formed between a slide surface and the capillary plane; one or more width locating blocks are provided at an outer edge of each depth locating face which is far away from the capillary plane; a vertical distance between the width locating blocks located on different depth locating faces matches to a width of the slide to play a stopping function; the bottom locating block is provided at a bottom of the depth locating face; the reservoir opening face is connected with an upper end of the capillary plane and forms an angle A1, and A1 is a plane angle of 1° to 175°; two sides of the reservoir opening face are each connected with one reservoir side face; the reservoir opening face and two reservoir side faces and a slide plane together constitute one reagent loading reservoir which is connected with the capillary gap, and a bottom of the capillary gap has a gap opening; a length of the slide cover plate corresponds to or is equal to that of the slide, one label dent is provided on each side of the reservoir side face which is attached to the slide plane, that is, upper ends of the two depth locating faces are each provided with one label dent, and when the label is stuck to the slide, the label dent provides enough space for containing a thickness of the label, enabling the slide cover plate to be pressed tight against the slide without being affected by whether the label is stuck to the slide; outer sides of the two reservoir side faces are provided with top stripes for enhancing a friction between the reservoir side face and the finger; a vertical distance between the capillary plane and the depth locating face is 0.01 to 0.5 mm, so that after the slide cover plate is pressed tight against the slide, one capillary gap having a spacing of 0.01 to 0.5 mm is formed between the slide surface and the capillary plane; and a thickness of the width locating block that is higher beyond the depth locating face is 0.1 to 1 mm; the bottom locating block is upward hook-like, and the bottom locating block and the width locating block together determine a relative position after the cover plate is pressed against the slide, and assist keeping the cover plate being pressed tight against the slide.

Further, after the slide assembly is inserted in the V-shape insertion slot, the slide is inclined or upright, with an angle between the slide and the vertical direction of 1° to 90°.

Further, the slide at least contains one biological specimen thereon.

Further, two ends of the slide rack are hung on two lateral sides facing toward each other of the container, so that a gap is provided between a bottom end of the slide assembly in the slide rack and a bottom of the container; the slide rack is provided with a plurality of integrated V-shape insertion slots which are upright or inclined, and the spring piece is fixed inside each V-shape insertion slot; the spring piece and the V-shape insertion slot of the slide rack can be an integrated connection structure, or can be configured as independent separation; when the independent separation is adopted, the spring piece is fixed inside the V-shape insertion slot by means of embedding or adhesion; when the slide assembly is inserted in the V-shape insertion slot, a surface of the cover plate presses the spring piece, and the spring piece plays a function of clamping the slide and the cover plate.

Further, the device comprises one or more individual containers, so as to simultaneously carry out the slide specimen processing at different temperatures, in different circumstances or in different operation procedures.

Further, the heating device adopts electrical bar heating, electrical wire heating, microwave heating, electromagnetic induction heating or circulating thermal medium heating; and the heating device and the container form a connected structure or a detachable structure.

Further, in a processing method using the above device for processing the slide specimen, the slide assembly that is assembled after the slide cover plate is pressed tight against the slide is immersed entirely or with a bottom thereof partially inserted in a hot solution in the container for heating, and even if there is evaporation during the heating, solution in a gap can still be automatically replenished by sucking liquid from a gap opening at the bottom.

Further, when the slide assembly is in a heat treatment, a heating medium in the container is heated to boiling, which boiling point serves as a controlled temperature of the heat treatment.

Further, it is assumed that during a test process, a required temperature maintaining time after a solution in the container starts boiling is $T2$; when the heating starts, the controller sets a heating power as K1 to perform a fast heating; during the heating, the thermocouple provides a feedback of a solution temperature at any moment; and when the temperature reaches to the boiling point, the controller sets the heating power as K2, keeps the solution boiling gently and activates timing simultaneously, and the heating is stopped when the timing reaches to $T2$.

Further, after testing and verifying the heating to the container, it only requires to set a time $T1$ for heating to boiling and the temperature maintaining time $T2$, without adjusting the time and power for heating through a feedback of the thermocouple.

Further, the controller automatically controls a feeding micropump to fill the container with liquid and a drainage micropump to discharge liquid from the container;

when the slide specimen processing needs the heat treatment, the feeding micropump fills the container with liquid in order to heat the slide specimen by cooking; and after the heat treatment, the drainage micropump pumps out the heating liquid or pumps out wastes, which are generated during the slide specimen processing.

Further, when a new reagent is added, the new reagent enters the gap from a reagent loading reservoir, the former reagent existing in the gap flows from the guiding opening at the bottom of the slide assembly and is replaced by the new reagent automatically; and it doesn't require steps of removing and draining the former reagent of the last step before adding the new reagent.

Further, it is assumed that the feeding micropump has a flow velocity of $V2$, the drainage micropump has a flow velocity of $V3$, and the container has a length of L and a width of W; during one operation process, a solution which is required to be added to the container has a depth of H, and then a value of the depth of the solution which is newly added can be set as H in the controller, and at this moment, the controller automatically calculates an operation time of the feeding micropump as $T3=L*W*H/V2$; when it requires to drain the solution having the depth of H out of the container, the controller automatically controls an operation time of the drainage micropump as $T3+\Delta t$, wherein $\Delta t$ is a set time margin, with a purpose of guaranteeing the liquid in the container to be drained off.

When the slide assembly of the present invention is in the heat treatment, the heating medium in the container is heated to boiling. The temperature of the heat treatment is controlled according to the boiling point of the heating medium, achieving uniformity, reliability and repeatability for the heat treatment. The slide remains at the same position without moving during the whole process of the slide specimen processing. When the slide assembly is in the heat treatment, a plurality of slide assemblies are heated in one same container at a temperature controlled by a single heating controller, rather than that each slide assembly is heated separately and independently temperature-controlled.

Controllers such as PIC MCU, MCU-51 or PLC controller are used. Power-on and power-off of a relay are controlled by the controller, thereby realizing start and stop of the heating function, and realizing control of opening and closing for the inlet and the outlet.

Compared with the prior art, the present invention has following advantages and technical effects:

A slide assembly is formed by assembling the slide cover plate of the present invention and the slide. There's one tiny gap at the middle of the slide assembly and a reagent loading reservoir above the tiny gap. A reagent fills the gap via the effects of gravity and capillary siphoning after the reagent is added to the reagent loading reservoir, and excess reagent flows from a gap opening at the bottom of the tiny gap. However, liquid in the gap will not be totally drained, which guarantees that the slide specimen is covered by the reagent. When the heat treatment is needed, a reagent or a heating medium is filled in the container for heating, the slide assemblies inserted in the insertion slots are immersed entirely or with bottoms partially immersed in the heating medium in the container for heating. Even if there is evaporation during the heating, owing to the effect of capillary siphoning, the liquid in the gap may also be automatically replenished by sucking liquid from the gap opening at the bottom of the slide assembly, guaranteeing that no drying of specimen takes place during the heat treatment. A heating time can be adjusted flexibly via a time adjustment window. The temperature in the container is observed any time via a temperature display screen. The present invention enables the slide specimen processing to be performed in one device during the whole process, without transferring the slide specimen halfway. The device of the present invention is further provided with devices for filling the heating medium in the container and discharging the heating medium and a waste liquid from the container, which reduce manual operation and intervention required during the slide processing.

Further preferably, the present invention may provide a plurality of individual containers which may carry out independent temperature control respectively, for simultaneously carrying out the slide specimen processing at different temperatures, or in different operation procedures.

When the designed slide assembly is placed inclined or upright (with an angle between 1° and 90°, and when a new reagent is added during the operation, the former reagent in the gap is replaced by the new reagent automatically and flows from a guiding opening at the bottom, without steps of removing and draining the initial liquid (reagent) on the slide before adding the new reagent. In the whole process of the slide specimen processing, there's no need to take or transfer the slide manually which enhances an efficiency of cleaning and simplifies the procedure.

BRIEF DESCRIPTION OF THE DRAWINGS

FIG. 3 shows a diagram of an assembly (slide assembly) of a slide and the cover plate in the embodiment.

FIG. 4a shows a front view of the slide assembly in FIG. 3.

FIG. 4b shows an A-A sectional view of the slide assembly in FIG. 3.

FIG. 4c shows an enlarged view of FIG. 4b.

FIG. 9 shows a diagram of the device shown in FIG. 8 with the slide rack and the slide assemblies placed in.

Figure 1:
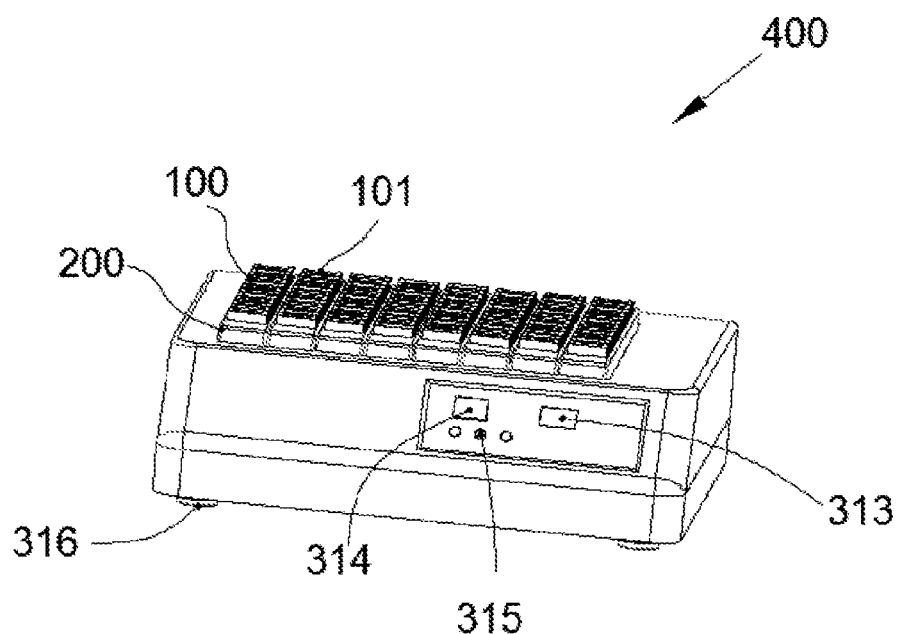
FIG. 1 shows a diagram of a device for processing a slide specimen in an embodiment.
Figure 2:
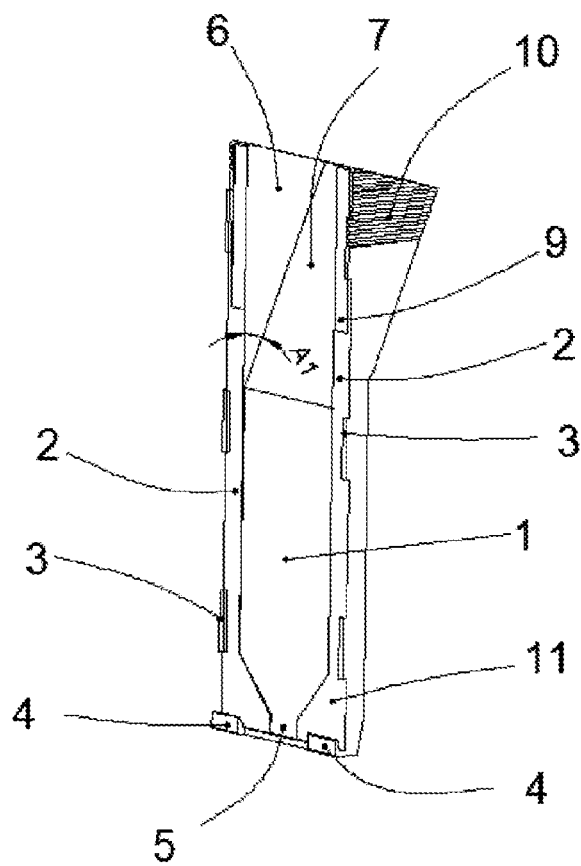
FIG. 2 shows a structural diagram of a slide cover plate in the embodiment.

In the figures: 301—container; 302—base; 303—heating device; 307—liquid outlet; 308—liquid inlet; 309—controller; 310—drainage micropump (magnetic valve); 311—feeding micropump; 312—thermocouple; 313—temperature display screen; 314—temperature maintaining time display window; 315—temperature maintaining time adjustment button; 316—support; 101—slide; 100—slide cover plate; 200—slide rack; 201—plate type spring; 202—supporting inclined wall; 203—insertion slot.

DETAILED DESCRIPTION OF THE PREFERRED EMBODIMENT

The present invention is further described below in combination with specific embodiments, but implementations and protection of the present invention are not limited by these.

As shown in FIG. 1 to FIG. 10, a device for processing a slide specimen of the present embodiment, mainly comprises components such as a container 301, a base 302, a heating device 303, a liquid outlet 307, a liquid inlet 308, a controller 309, a drainage pump 310, a feeding pump 311, a thermocouple 312, a temperature display screen 313, a time adjustment window 314, a slide cover plate 601, a slide 101 and a slide rack 602.

Figure 5A:
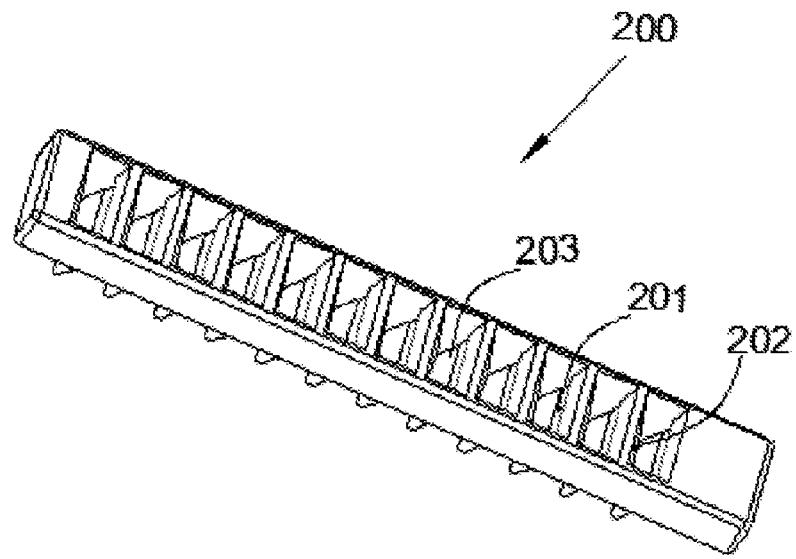
FIG. 5a shows a diagram of a slide rack in the embodiment.
Figure 5B:
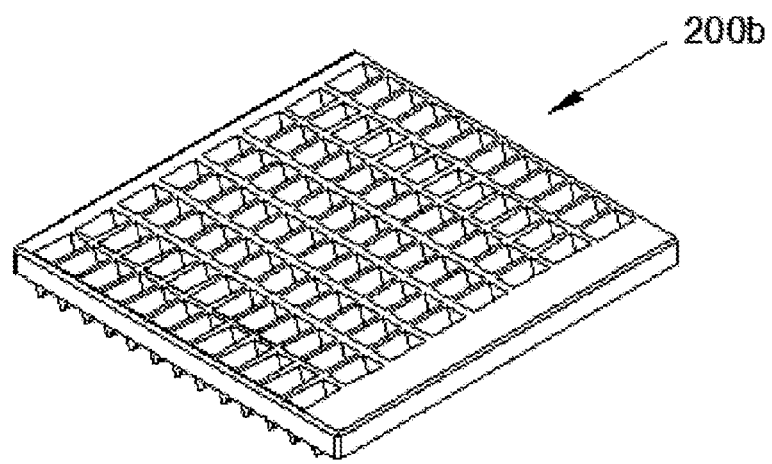
FIG. 5b shows a diagram of a slide rack having multi-column insertion slots in the embodiment.
Figure 6:
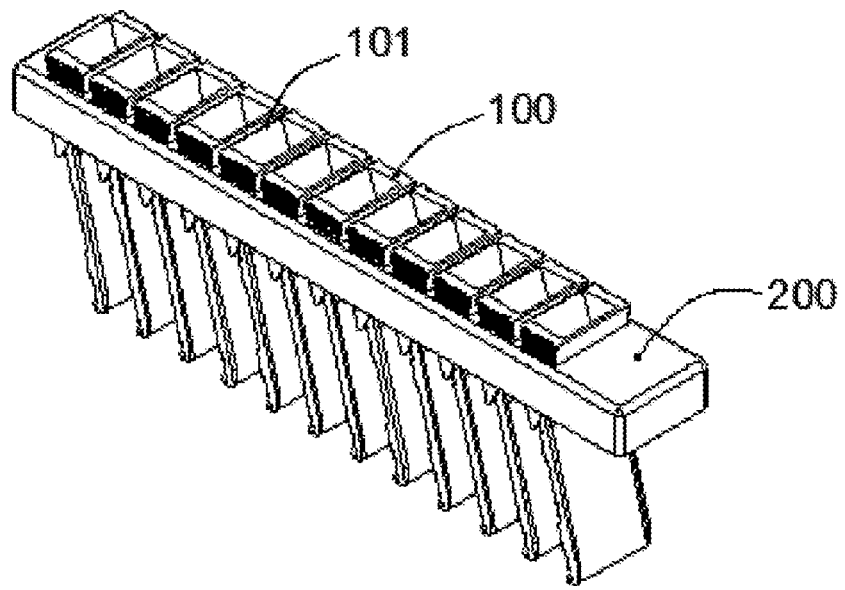
FIG. 6 shows a diagram of a slide rack inserted with the slide assemblies in the embodiment.
Figure 7:
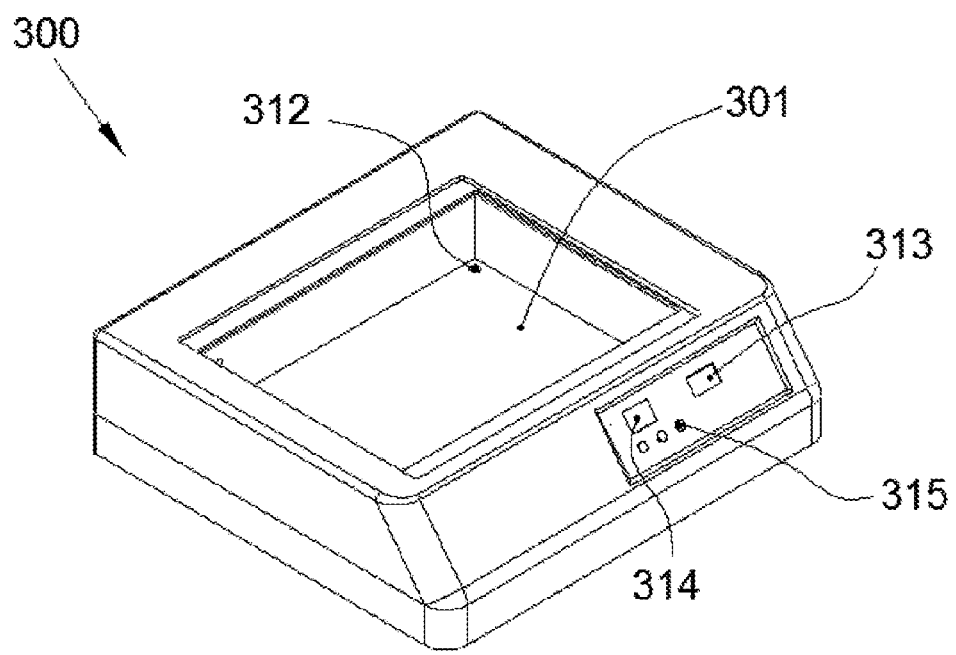
FIG. 7 shows a rear diagram of the device for processing the slide specimen from which the slide rack is removed in the embodiment.
Figure 8:
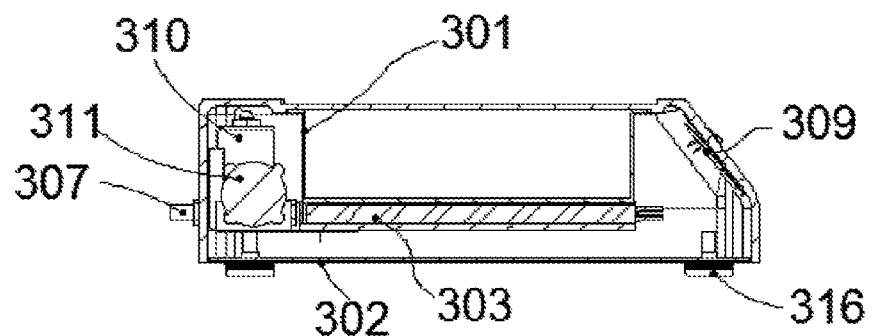
FIG. 8 shows a sectional view of the device shown in FIG. 7.

As shown in FIGS. 5a and 5b, the slide rack is a slide rack with single-column insertion slots 200 or a slide rack with multi-column insertion slots 200b.

As shown in FIG. 3, the slide cover plate 100 fits with the slide 101 to assemble a set of slide assembly 103 for specimen processing.

In FIG. 1, one or more slide racks are hung in the container 301; each column of the slide rack is provided with one or more V-shape insertion slots 203, and the V-shape insertion slots 203 in a same column are arranged in line; a spring piece 201 is provided inside each V-shape insertion slot; an outline of an upper end of the slide assembly matches with the V-shape insertion slot, and the slide assembly 103 is inserted along the V-shape insertion slot of the slide rack; back of the slide cover plate 100 presses the spring piece 201, and a spring pressure is generated to clamp the slide 101 and the slide cover plate 100.

The heating device 303 is located above the base 302 and below the container 301; the controller 309 controls a heating operation of the heating device performed on the container 301; the thermocouple 312 is positioned inside the container; the thermocouple 312 performs a real-time sense on a temperature in the container 301, and transfers a sensed temperature information to the controller 309 to adjust a power output of the heating device, and then to adjust the temperature; the temperature display screen 313 shows the temperature inside the container; the temperature maintaining time adjustment button 315 can adjust and set a time for the temperature maintaining; and the temperature maintaining time display window 314 shows a required time for the temperature maintaining.

The liquid inlet 308 allows a heating medium or reagent stored in an external container to be added to the container 301 quantitatively when required; the liquid outlet 307 allows the heating medium or liquid in the container 301 to be discharged from the container; and the liquid inlet and the liquid outlet can be connected with a micropump or a magnetic valve, and the controller 309 controls the micropump or the magnetic valve to open or close.

The slide cover plate 100 has a rectangular plane slot, so that one capillary gap is formed between the slide 101 and the cover plate after the slide 101 is attached to the cover plate; a slide specimen section is stuck on a surface of the slide 101 in the capillary gap, and a loading liquid enters the capillary gap through a reagent loading reservoir 102 formed between the cover plate 100 and the slide 101, and covers evenly on the slide specimen. Owing to the effects of gravity and capillary siphoning, the loading liquid enters the capillary gap through the reagent loading reservoir 102 formed between the cover plate and the slide 101, and covers on the slide specimen.

As shown in FIG. 3 and FIGS. 4a to 4c, the cover plate comprises a capillary plane 1, a depth locating face 2, a width locating block 3, a bottom locating block 4, a reservoir side face 6 and a reservoir opening face 7; two depth locating faces 2 are provided above two lateral sides facing toward each other of the capillary plane 1, and the capillary plane 1 is parallel to the depth locating faces; portions of a plane of the slide which are close to edges of two sides are attached to the depth locating faces 2, so that one capillary gap is formed between a slide surface and the capillary plane 1; one or more width locating blocks 3 are provided at an outer edge of each depth locating face 2 which is far away from the capillary plane 1; a vertical distance between the width locating blocks 3 located on different depth locating faces 2 matches to a width of the slide to play a stopping function; the bottom locating block 4 is provided at a bottom of the depth locating face 2; the reservoir opening face 7 is connected with an upper end of the capillary plane 1 and forms an angle A1, and A1 is a plane angle of 1° to 175°; two sides of the reservoir opening face 7 are each connected with one reservoir side face 6; the reservoir opening face 7 and two reservoir side faces 6 and a slide plane together constitute one reagent loading reservoir which is connected with the capillary gap, and a bottom of the capillary gap has a gap opening; a length of the slide cover plate corresponds to or is equal to that of the slide, one label dent 9 is provided on each side of the reservoir side face 6 which is attached to the slide plane, that is, upper ends of the two depth locating faces 2 are each provided with one label dent 9, and when the label is stuck to the slide, the label dent provides enough space for containing a thickness of the label, enabling the slide cover plate to be pressed tight against the slide without being affected by whether the label is stuck to the slide; outer sides of the two reservoir side faces 6 are provided with top stripes 10 for enhancing a friction between the reservoir side face 6 and the finger; a vertical distance between the capillary plane 1 and the depth locating face 2 is 0.01 mm to 0.5 mm, so that after the slide cover plate is pressed tight against the slide, one capillary gap having a spacing of 0.01 mm to 0.5 mm is formed between the slide surface and the capillary plane 1; and a thickness of the width locating block 3 that is higher beyond the depth locating face 2 is 0.1 mm to 1 mm; the bottom locating block 4 is upward hook-like, and the bottom locating block 4 and the width locating block 3 together determine a relative position after the cover plate is pressed against the slide, and assist keeping the cover plate being pressed tight against the slide. The V-shape insertion slot structurally fits with the slide assembly, enabling the container to contain more slide assemblies. When in use, it only requires the fingers to clamp the top stripes portions of two reservoir side faces and the slide, so that it is easy to insert the slide assembly into the insertion slot. Uneven stressing generating when a top end of the slide is pressed and separation of the slide from the slide cover plate owing to deviation of a stressing direction are prevented, guaranteeing formation and accuracy of the capillary gap and making the operation simpler and faster. Besides, arrangement of the slide assemblies can be tighter, which further saves space and enhances a processing efficiency.

As an embodiment, all components are made of a material that is able to remain non-deformed or not-soften when heated to 80° C. or above. After the slide assembly 103 is inserted in the V-shape insertion slot, the slide is inclined or upright, and an angle between the slide and the vertical direction is 1° to 90°. The slide at least contains one biological specimen thereon.

Figure 9:
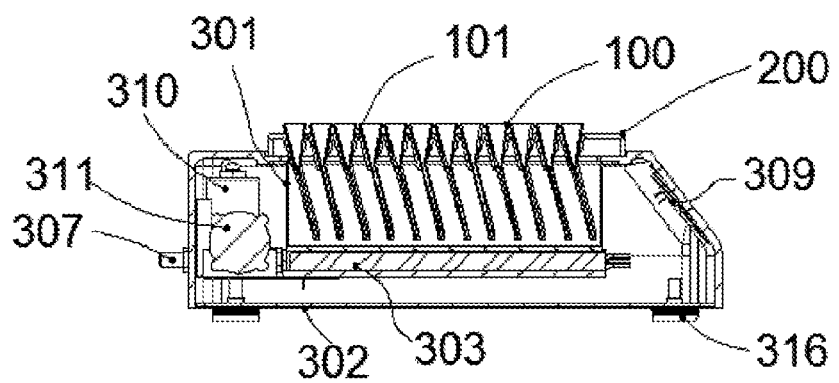
Figure 10:
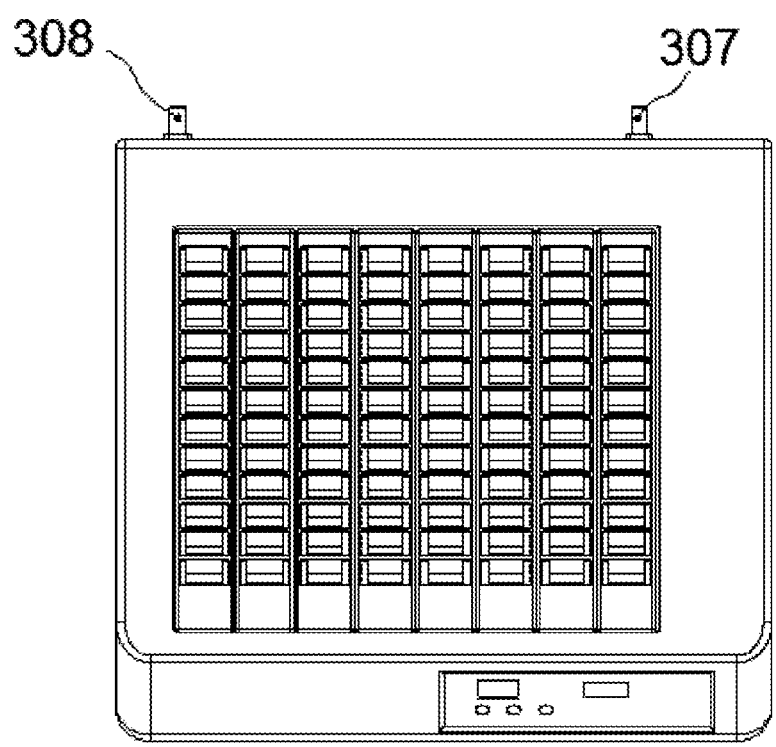
FIG. 10 shows a diagram of the device shown in FIG. 7 after the slide rack having multi-column insertion slots is placed in the device.

As shown in FIG. 9, two ends of the slide rack are hung on two lateral sides facing toward each other of the container, so that a gap is provided between a bottom end of the slide assembly in the slide rack and a bottom of the container; the slide rack is provided with a plurality of integrated V-shape insertion slots 203 which are upright or inclined, and the spring piece 201 is fixed inside each V-shape insertion slot 203; the spring piece 201 and the V-shape insertion slot 203 of the slide rack can be an integrated connection structure, or can be configured as independent separation; when the independent separation is adopted, the spring piece 201 is fixed inside the V-shape insertion slot 203 by means of embedding or adhesion; when the slide assembly is inserted in the V-shape insertion slot 203, a surface of the cover plate 100 presses the spring piece 201, and the spring piece plays a function of clamping the slide 101 and the cover plate 100.

A device for processing slide specimen of the embodiment can comprise one or more individual containers, so as to simultaneously carry out the slide specimen processing at different temperatures, in different circumstances or in different operation procedures. The heating device adopts electrical bar heating, electrical wire heating, microwave heating, electromagnetic induction heating or circulating thermal medium heating; and the heating device 303 and the container 301 form a connected structure or a detachable structure.

A processing method using the device for processing slide specimen of the embodiment: the slide assembly 103 that is assembled after the slide cover plate is pressed tight against the slide is immersed entirely or with a bottom thereof partially inserted in a hot solution in the container for heating, and even if evaporation generates during the heating, solution in a gap can also be automatically replenished by sucking liquid from a gap opening at the bottom. When the slide assembly is in a heat treatment, a controlled temperature of the heat treatment may be reached by heating the heating medium in the container to boiling.

It is assumed that during a test process, a required temperature maintaining time after a solution in the container 301 starts boiling is T2; when the heating starts, the controller sets a heating power as K1 to perform a fast heating; during the heating, the thermocouple (312) provides a feedback of a solution temperature at any moment; and when the temperature reaches to the boiling point, the controller sets the heating power as K2, keeps the solution boiling gently and activates timing simultaneously, and the heating is stopped when the timing reaches to T2.

As an embodiment, after testing and verifying the heating to the container, it only requires to set a time T1 for heating to boiling and the temperature maintaining time T2, without adjusting the time and power for heating through a feedback of the thermocouple.

In the embodiment, when a new reagent is added, the new reagent enters the gap from a reagent loading reservoir, the former reagent existing in the gap flows from the guiding opening at the bottom of the slide assembly and liquid in the gap is thus replaced by the newly added reagent automatically; and it does not require steps of removing and draining the former reagent of the previous step before adding the new reagent. As an embodiment, controllers such as PIC MCU, MCU-51 or PLC controller are used. Start and stop of the feeding micropump and the drainage micropump, as well as start and stop of the heating device and a power output during the heating, are controlled by the power-on and power-off of a relay which is controlled by the controller.

The controller automatically controls a feeding micropump to fill the container with liquid and a drainage micropump to discharge liquid from the container; when the slide specimen processing needs the heat treatment, the feeding micropump fills the container with liquid in order to heat the slide specimen by cooking; and after the heat treatment, the drainage micropump pumps the heating liquid out or pumps out wastes which are generated during the slide specimen processing. It is assumed that the feeding micropump has a flow velocity of V2, the drainage micropump has a flow velocity of V3, and the container has a length of L and a width of W; during one operation process, a solution which is required to be added to the container has a depth of H, and then a value of the depth of the solution which is newly added can be set as H in the controller, and at this moment, the controller automatically calculates an operation time of the feeding micropump 311 as T3=L*W*H/V2; when it requires to drain the solution having the depth of H out of the container, the controller automatically controls an operation time of the drainage micropump 310 as T3+Δt, wherein Δt is a set time margin, with a purpose of guaranteeing the liquid in the container to be drained off.

When the slide assembly of the present invention is in the heat treatment, the heating medium in the container may be heated to boiling. The temperature of the heat treatment is controlled according to the boiling point of the heating medium, achieving uniformity, reliability and repeatability for the heat treatment. The slide remains at the same position without moving during the whole process of the slide specimen processing. When the slide assembly is in the heat treatment, a plurality of slide assemblies are heated in one same container at a temperature controlled by a single heating controller, rather than that each slide assembly is heated separately and independently temperature-controlled.

According to the disclosure and teaching of the above description, those skilled in the art of the present invention may further modify and alter the above implementations. Therefore, the present invention is not limited by the above disclosure and the described specific implementations, and some alteration and modification of the present invention shall also fall into the scope of protection as claimed by the claims of the present invention

What is claimed is:

1. A device for processing a slide specimen, comprising: a container, a base, a heating device, a slide cover plate, a slide, a slide rack, a liquid outlet, a liquid inlet, a controller, a thermocouple, a temperature display screen, a temperature maintaining time display window and a temperature maintaining time adjustment button; the slide rack is a slide rack with single-column insertion slots or a slide rack with multi-column insertion slots;
   wherein the slide cover plate fits with the slide to assemble a set of slide assembly for specimen processing,
   wherein one or more slide racks are hung in the container; each column of the slide rack is provided with one or more V-shape insertion slots, and the V-shape insertion slots in a same column are arranged in line; a spring piece is provided inside each V-shape insertion slot; an outline of an upper end of the slide assembly matches with the V-shape insertion slot, and the slide assembly is inserted along the V-shape insertion slot of the slide rack; back of the slide cover plate presses the spring piece, and a spring pressure is generated to clamp the slide and the slide cover plate,
   wherein the heating device is located above the base and below the container; the controller controls a heating operation of the heating device performed on the container; the thermocouple is positioned inside the container; the thermocouple performs a real-time sense on a temperature in the container, and transfers a sensed temperature information to the controller to adjust a power output of the heating device, and then to adjust the temperature; the temperature display screen shows the temperature inside the container; the temperature maintaining time adjustment button can adjust and set a time for the temperature maintaining; and the temperature maintaining time display window shows a required time for the temperature maintaining,
   wherein the liquid inlet allows a heating medium or reagent stored in an external container to be added to the container quantitatively when required; the liquid outlet allows the heating medium or the reagent in the container to be discharged from the container; and the liquid inlet and the liquid outlet can be connected with a micropump or a magnetic valve, and the controller controls the micropump or the magnetic valve to open or close.

2. The device for processing the slide specimen according to claim 1, wherein the slide cover plate has a rectangular plane slot, so that one capillary gap is formed between the slide and the cover plate after the slide is attached to the cover plate; a slide specimen section is stuck on a surface of the slide in the capillary gap, and a loading liquid enters the capillary gap through a reagent loading reservoir formed between the cover plate and the slide, and covers evenly on the slide specimen.

3. The device for processing the slide specimen according to claim 2, wherein the cover plate comprises a capillary plane, a depth locating face, a width locating block, a bottom locating block, a reservoir side face and a reservoir opening face; two depth locating faces are provided above two lateral sides facing toward each other of the capillary plane, and the capillary plane is parallel to the depth locating faces; portions of a plane of the slide which are close to edges of two sides are attached to the depth locating faces, so that one capillary gap is formed between a slide surface and the capillary plane; one or more width locating blocks are provided at an outer edge of each depth locating face which is far away from the capillary plane; a vertical distance between the width locating blocks located on different depth locating faces matches to a width of the slide to play a stopping function; the bottom locating block is provided at a bottom of the depth locating face; the reservoir opening face is connected with an upper end of the capillary plane and forms an angle A1, and A1 is a plane angle of 1° to 175°; two sides of the reservoir opening face are each connected with one reservoir side face; the reservoir opening face and two reservoir side faces and a slide plane together constitute one reagent loading reservoir which is connected with the capillary gap, and a bottom of the capillary gap has a gap opening; a length of the slide cover plate corresponds to or is equal to that of the slide, one label dent is provided on each side of the reservoir side face which is attached to the slide plane, that is, upper ends of the two depth locating faces are each provided with one label dent, and when the label is stuck to the slide, the label dent provides enough space for containing a thickness of the label, enabling the slide cover plate to be pressed tight against the slide without being affected by whether the label is stuck to the slide; outer sides of the two reservoir side faces are provided with top stripes for enhancing a friction between the reservoir side face and the finger; a vertical distance between the capillary plane and the depth locating face is 0.01 to 0.5 mm, so that after the slide cover plate is pressed tight against the slide, one capillary gap having a spacing of 0.01 to 0.5 mm is formed between the slide surface and the capillary plane; and a thickness of the width locating block that is higher beyond the depth locating face is 0.1 to 1 mm; the bottom locating block is upward hook-like, and the bottom locating block and the width locating block together determine a relative position after the cover plate is pressed against the slide, and assist keeping the cover plate being pressed tight against the slide.

4. The device for processing the slide specimen according to claim 1, wherein after the slide assembly is inserted in the V-shape insertion slot, the slide is inclined or upright, and an angle between the slide and the vertical direction is 1° to 90°.

5. The device for processing the slide specimen according to claim 1, wherein the slide at least contains one biological specimen thereon.

6. The device for processing the slide specimen according to claim 1, wherein two ends of the slide rack are hung on two lateral sides facing toward each other of the container, so that a gap is provided between a bottom end of the slide assembly in the slide rack and a bottom of the container; the slide rack is provided with a plurality of integrated V-shape insertion slots which are upright or inclined, and the spring piece is fixed inside each V-shape insertion slot; the spring piece and the V-shape insertion slot of the slide rack can be an integrated connection structure, or can be configured as independent separation; when the independent separation is adopted, the spring piece is fixed inside the V-shape insertion slot by means of embedding or adhesion; when the slide assembly is inserted in the V-shape insertion slot, a surface of the cover plate presses the spring piece, and the spring piece plays a function of clamping the slide and the cover plate.

7. The device for processing the slide specimen according to claim 1, wherein the device comprises one or more individual containers, so as to simultaneously carry out the slide specimen processing at different temperatures, in different circumstances or in different operation procedures.

8. The device for processing the slide specimen according to claim 1, wherein the heating device adopts electrical bar heating, electrical wire heating, microwave heating, electromagnetic induction heating or circulating thermal medium heating; and the heating device and the container form a connected structure or a detachable structure.

9. A processing method using the device for processing the slide specimen according to claim 1, wherein the slide assembly that is assembled after the slide cover plate is pressed tight against the slide is immersed entirely or with a bottom thereof partially inserted in a hot solution in the container for heating, and during the heating, even if there is evaporation, solution in a gap can also be automatically replenished by sucking liquid from a gap opening at the bottom.

10. The processing method according to claim 9, wherein when the slide assembly is in a heat treatment, a heating medium in the container is heated to boiling, which a boiling point serves as a controlled temperature of the heat treatment.

11. The processing method according to claim 9, wherein it is assumed that during a test process, a required temperature maintaining time after a solution in the container starts boiling is T2; when the heating starts, the controller sets a heating power as K1 to perform a fast heating; during the heating, the thermocouple provides a feedback of a solution temperature at any moment; and when the temperature reaches to the boiling point, the controller sets the heating power as K2, keeps the solution boiling gently and activates timing simultaneously, and the heating is stopped when the timing reaches to T2.

12. The processing method according to claim 9, wherein after testing and verifying the heating to the container, it only requires to set a time T1 for heating to boiling and the temperature maintaining time T2, without adjusting the time and power for heating through a feedback of the thermocouple.

13. The processing method according to claim 9, wherein the controller automatically controls a feeding micropump to fill the container with liquid and a drainage micropump to discharge liquid from the container; when the slide specimen processing needs the heat treatment, the feeding micropump fills the container with liquid in order to heat the slide specimen by cooking; and after the heat treatment, the drainage micropump pumps out the heating liquid, or pumps out wastes which are generated during the slide specimen processing.

14. The processing method according to claim 13, wherein it is assumed that the feeding micropump has a flow velocity of V2, the drainage micropump has a flow velocity of V3, and the container has a length of L and a width of W; during one operation process, a solution which is required to be added to the container has a depth of H, and then a value of the depth of the solution which is newly added can be set as H in the controller, and at this moment, the controller automatically calculates an operation time of the feeding micropump as $T3=L*W*H/V2$; when it requires to drain the solution having the depth of H out of the container, the controller automatically controls an operation time of the drainage micropump as $T3+\Delta t$, wherein $\Delta t$ is a set time margin, with a purpose of guaranteeing the liquid in the container to be drained off.

15. The processing method according to claim 9, wherein when a new reagent is added, the new reagent enters the gap from a reagent loading reservoir, the former reagent existing in the gap flows from the guiding opening at the bottom of the slide assembly and liquid in the gap is thus replaced by the newly added reagent automatically; and it doesn't require steps of removing and draining the former reagent of the last step before adding the new reagent.

\* \* \* \* \*